(12) United States Patent
Wardle et al.

(10) Patent No.: US 10,492,949 B2
(45) Date of Patent: Dec. 3, 2019

(54) SINGLE OPERATOR DEVICE FOR DELIVERING AN OCULAR IMPLANT

(71) Applicant: IVANTIS, INC., Irvine, CA (US)

(72) Inventors: John Wardle, San Clemente, CA (US); Andrew T. Schieber, Irvine, CA (US)

(73) Assignee: IVANTIS, INC., Irvine, CA (US)

( * ) Notice: Subject to any disclaimer, the term of this patent is extended or adjusted under 35 U.S.C. 154(b) by 169 days.

(21) Appl. No.: 15/632,130

(22) Filed: Jun. 23, 2017

(65) Prior Publication Data
US 2017/0290705 A1    Oct. 12, 2017

Related U.S. Application Data

(62) Division of application No. 12/833,852, filed on Jul. 9, 2010, now Pat. No. 9,693,899.

(60) Provisional application No. 61/224,156, filed on Jul. 9, 2009.

(51) Int. Cl.
*A61F 9/007* (2006.01)
*A61F 9/00* (2006.01)

(52) U.S. Cl.
CPC ........ *A61F 9/00781* (2013.01); *A61F 9/0017* (2013.01)

(58) Field of Classification Search
CPC ...... A61F 9/00781; A61F 9/0017; A61F 9/00; A61F 9/007; A61M 27/002
See application file for complete search history.

(56) References Cited

U.S. PATENT DOCUMENTS

| 703,296 A | 6/1902 | Arnold |
| 1,601,709 A | 10/1926 | Windom |
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Berlin et al.; U.S. Appl. No. 15/868,904 entitled "Methods and systems for OCT guided glaucoma surgery," filed Jan. 11, 2018.

(Continued)

*Primary Examiner* — Anh T Dang
(74) *Attorney, Agent, or Firm* — Shay Glenn LLP

(57) ABSTRACT

An ocular implant delivery system is provided with a number of features. In some embodiments, the delivery system comprises a rotation mechanism configured to rotate and orient a cannula of the system, and an advancement mechanism configured to advance and retract an ocular implant through the delivery system and into an eye of a patient. In some embodiments, the cannula is sized and configured to be inserted into Schlemm's canal of the eye. The ocular implant is configured to maintain its orientation within the delivery system as the cannula is rotated. In some embodiments, the ocular implant automatically disengages the delivery system when it is advanced beyond a distal tip of the delivery system. Methods of implanting an ocular implant are also provided.

13 Claims, 12 Drawing Sheets

(56) References Cited

U.S. PATENT DOCUMENTS

| | | |
|---|---|---|
| 3,858,577 A | 1/1975 | Bass et al. |
| 3,884,236 A | 5/1975 | Krasnov |
| 3,948,271 A | 4/1976 | Akiyama |
| 3,982,541 A | 9/1976 | L'Esperance |
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A * | 3/1992 | Ritch ............... A61F 9/00781 604/294 |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |

(56) References Cited

U.S. PATENT DOCUMENTS

| | | |
|---|---|---|
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Schieber et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,775,729 B2 | 10/2017 | McClain et al. |
| 9,820,883 B2 | 11/2017 | Berlin |
| 9,833,357 B2 | 12/2017 | Berlin |
| 10,159,601 B2 | 12/2018 | Berlin |
| 10,335,314 B2 | 7/2019 | Berlin |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |

(56) References Cited

U.S. PATENT DOCUMENTS

| | | |
|---|---|---|
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2013/0182223 A1 | 7/2013 | Wardle et al. |
| 2014/0066821 A1 | 3/2014 | Freidland et al. |
| 2014/0066831 A1 | 3/2014 | Silvestrini et al. |
| 2015/0119787 A1 | 4/2015 | Wardle et al. |
| 2015/0282982 A1 | 10/2015 | Schieber et al. |
| 2015/0290033 A1 | 10/2015 | Wardle et al. |
| 2015/0366710 A1 | 12/2015 | Schieber et al. |
| 2016/0051406 A1 | 2/2016 | Wardle et al. |
| 2016/0220417 A1 | 8/2016 | Schieber et al. |

(56) References Cited

U.S. PATENT DOCUMENTS

| | | |
|---|---|---|
| 2016/0250072 A1 | 9/2016 | Wardle et al. |
| 2017/0143541 A1 | 5/2017 | Badawi et al. |
| 2017/0156848 A1 | 6/2017 | Schieber |
| 2017/0172794 A1 | 6/2017 | Varner et al. |
| 2017/0202708 A1 | 7/2017 | Berlin |
| 2017/0239272 A1 | 8/2017 | Ambati et al. |
| 2017/0252212 A1 | 9/2017 | Euteneuer et al. |
| 2017/0281409 A1 | 10/2017 | Haffner et al. |
| 2018/0369017 A1 | 12/2018 | Schieber et al. |

FOREIGN PATENT DOCUMENTS

| | | |
|---|---|---|
| DE | 4226476 C1 | 8/1993 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 1732484 B1 | 8/2017 |
| EP | 1740153 B2 | 8/2017 |
| EP | 3205333 A1 | 8/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2010509003 A | 3/2010 |
| JP | 2011502649 A | 1/2011 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/13627 A1 | 3/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |

OTHER PUBLICATIONS

Cambridge Dictionary; Sensor (definition); 2 pages; retrived from the internet (http://dictionary.cambridge.org/define.asp?dict=CALD &key=71811 >) on Aug. 14, 2018.

Dietlein et al.; Morphological variability of the trabecular meshwork in glaucoma patients: implications for non-perforating glaucoma surgery; British Journal of Ophthalmology; 84(12); pp. 1354-1359; Dec. 2000.

Huang et al.; Optical coherence tomography; Science; 254(5035); pp. 1178-1181; 12 pages. (Author Manuscript); Nov. 1991.

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.

Lee et al.; Short-pulsed neodymium—YAG laser trabeculotomy. An in vivo morphological study in the human eye; Investigative Ophthalmology and Visual Science; 29(11); pp. 1698-1707; Nov. 1988.

Macmilla Online Dictionary; Detector (definition); Macmilla on Line Dictionary; 2 pages; retrived from the internet (https://www.macmillandictionary.com/dictionary/british/detector) on Aug. 14, 2018.

Nakamura et al.; Femtosecond laser photodisruption of primate trabecular meshwork: an ex vivo study; Investigative Ophthalmology and Visual Science; 50(3); pp. 1198-1204; Mar. 2009.

Owen; A moving-mirror gonioscope for retinal surgery; British Journal of Ophthalmology; 61(3); pp. 246-247; Mar. 1977.

Oxford Dictionaries; Detector (definition); 1 page; retrieved from the internet (https://en.oxforddictionaries.com/definition/detector) on Aug. 14, 2018.

Oxford Dictionaries; Sensor (definition); 1 page; retrieved from te Internet (http://www.askoxford.com/concise_oed/sensor?view=uk>) on Aug. 14, 2018.

Radhakrishnan et al.; Real-time optical coherence tomography of the anterior segment at 1310 nm; Archives of Opthhalmology; 119(8); pp. 1179-1185; Aug. 2001.

Toyran et al.; Femtosecond laser photodisruption of human trabecular meshwork: an in vitro study; Experimental Eye Research; 81(3); pp. 298-305; Sep. 2005.

Van Meter et al.; U.S. Appl. No. 15/751,886 entitled "Ocular implant with pressure sensor and delivery system," filed Feb. 12, 2018.

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Kirkness et al.; The Use of Silicone Drainage Tubing to Control Post-Keratoplasty Glaucoma; Eye; 2 (pt 5); pp. 583-590; Apr. 1988.

Lee et al.; Aqueous-venous shunt and intraocular pressure. Preliminary report of animal studies; Investigative Ophthalmology; vol. 5; No. 1; pp. 59-64; Feb. 1966.

Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Molteno et al.; Long Tube Implants in the Management of Glaucoma; SA Medical Journal; 26; pp. 1062-1066; Jun. 1976.

Molteno; New implant for drainage in glaucoma; Brit. J. Ophthal; 53; pp. 606-615; Sep. 1969.

Moses, Robert; The effect of intraocular pressure on resistance to outflow; Survey of Ophthalmology; vol. 22; No. 2; pp. 88-100; Sep.-Oct. 1977.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

(56) References Cited

OTHER PUBLICATIONS

Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Wilcox et al.; Hypothesis for Improving Accessory Filtration by Using Geometry; Journal of Glaucoma; 3; pp. 244-247; Fall 1994.
Berlin; U.S. Appl. No. 16/404,530 entitled "Delivery system and method of use for the eye," filed May 6, 2019.

\* cited by examiner

SINGLE OPERATOR DEVICE FOR DELIVERING AN OCULAR IMPLANT

CROSS REFERENCE TO RELATED APPLICATIONS

This application is a division of U.S. patent application Ser. No. 12/833,852, filed Jul. 9, 2010, now U.S. Pat. No. 9,693,899; which application claims the benefit under 35 U.S.C. 119 of U.S. Provisional Patent Application No. 61/224,156, filed Jul. 9, 2009, titled "Single Operator Device for Delivering an Ocular Implant". These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye and delivery systems for such devices. More particularly, the present invention relates to delivery system for devices that facilitate the transfer of fluid from within one area of the eye to another area of the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. Nos. 6,450,984; 6,450,984). Delivery and deployment systems for some glaucoma implants are described, e.g., in US 2007/0191863 and US 2007/0010827. Surgical devices for accessing Schlemm's canal are described, e.g., in US 2007/0073275 and US 2006/0149194.

SUMMARY OF THE INVENTION

In one embodiment, an ocular implant delivery system comprises a housing, a cannula coupled to the housing, the cannula sized and configured for insertion into Schlemm's canal of a human eye, a delivery mechanism disposed on the housing, the delivery mechanism configured to advance and retract an ocular implant within the cannula, and an orientation mechanism disposed on the housing, the orientation mechanism configured to control rotation of the cannula, wherein the ocular implant maintains its orientation with respect to the cannula when the cannula is rotated.

In some embodiments, the ocular implant delivery system further comprises a push tube slidably disposed within the cannula and coupled to the delivery mechanism. The ocular implant can be coupled to a distal portion of the push tube. In some embodiments, an interlocking finger of the implant is coupled to a finger receptacle on the push tube.

In another embodiment, the ocular implant delivery system further comprises a core shaft disposed within the ocular implant. The core shaft or core cable can be configured to align with an interior diameter of the ocular implant so as to prevent any sharp edges or holes of the implant from engaging tissue during implantation.

In one embodiment of the delivery system, the relative locations of the delivery mechanism and the orientation mechanism on the housing allow control over advancement and retraction of the ocular implant and rotation of the cannula with a single hand.

In another embodiment, the ocular implant is configured to automatically disengage from the ocular implant delivery system when it is advanced beyond a distal tip of the cannula. In some embodiments, the ocular implant is pre-biased to assume an expanded configuration. When the implant is advanced beyond the tip of the cannula, the implant can expand so as to disengage the delivery system (e.g., disengage a push tube).

In one embodiment, the ocular implant delivery system further comprises a core cable having a locking key, the locking key being configured to engage the ocular implant.

A method of delivering an implant into an eye of a patient is provided, comprising inserting a delivery device into the eye, advancing the implant into the eye through the delivery device, and expanding the implant to disengage the implant from the delivery device.

In some embodiments, the inserting step further comprises inserting a cannula into Schlemm's canal of the eye.

Another embodiment of the method further comprises the step of adjusting an orientation of the cannula with an orientation mechanism to align the cannula with a curvature of Schlemm's canal.

In some embodiments of the method, the advancing step and the adjusting step are achieved with a single-hand of a user.

The advancing step of the method can further comprise advancing the implant with a wheel disposed on the delivery device. In another embodiment, the advancing step further comprises advancing the implant into the eye past a distal tip of the delivery device. In an additional embodiment, the implant automatically expands to disengage itself from the delivery device when it is advanced past the distal tip of the delivery device.

In some embodiments, the expanding step further comprises expanding the implant to disengage an interlocking component of the implant from an interlocking component of the delivery device. The interlocking component of the delivery device can be an interlocking component of a push tube, for example. In another embodiment, the interlocking component of the delivery device can be an interlocking component of a core cable.

In some embodiments of the method, the advancing step further comprises advancing the implant into the eye with a push tube.

Alternatively, the advancing step can further comprise advancing the implant into the eye with a core cable. In one embodiment, the method can further comprise removing the core cable from the implant after expanding the implant.

In another embodiment, the implant is inserted into a suprachoroidal space.

Another method of implanting an ocular implant into Schlemm's canal of an eye is provided, comprising rotating an orientation mechanism of a delivery device to align a cannula with Schlemm's canal, advancing the cannula through a corneal incision and into the eye, piercing Schlemm's canal with the cannula, controlling an advancement mechanism of the delivery system with a first hand to advance the ocular implant from the delivery system into Schlemm's canal, holding a gonioscope with a second hand during the controlling step to visualize implantation of the ocular implant into Schlemm's canal, and automatically disengaging the ocular implant from the delivery system when the ocular implant is advanced beyond a distal tip of the cannula.

In some embodiments, the method further comprises expanding the ocular implant in the eye to disengage the ocular implant from the delivery system.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

The devices, systems, and methods described herein may aid in the treatment of glaucoma. The implantable ocular devices described herein may be inserted into Schlemm's canal, the trabecular meshwork, the suprachoroidal space, and/or the anterior chamber of the eye to facilitate the outflow of aqueous humor from the anterior chamber. When in place within the eye, the implantable devices can support trabecular meshwork tissue and/or Schlemm's canal tissue, and can provide for improved communication between the anterior chamber and Schlemm's canal (via the trabecular meshwork), between pockets or compartments along Schlemm's canal, and/or the suprachoroidal space.

The systems described herein may include delivery devices for delivering implantable devices into Schlemm's canal, the trabecular meshwork, the suprachoroidal space, and/or the anterior chamber of the eye. The delivery devices described herein may be configured to advance, retract, and deploy the implantable device precisely and predictably by a single physician or surgeon using the motion of a single finger. The delivery device may selectively engage the implantable device allowing the device to be advanced and retracted before implantation within the eye. The delivery devices described herein may also be configured to rotate a bent portion of the delivery device to align with the curvature of the iris of the eye.

Figure 1:
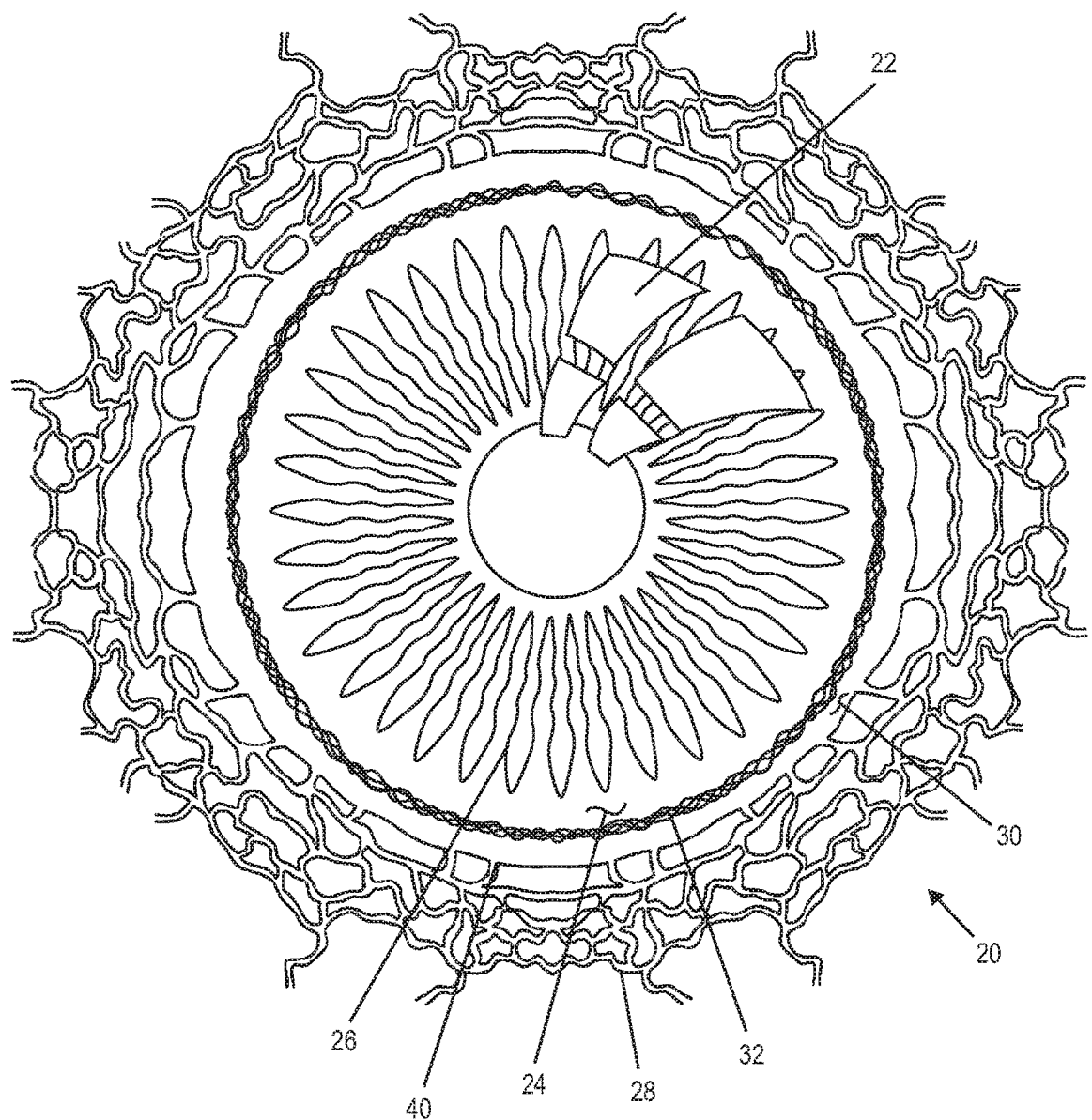
FIG. 1 is a schematic drawing of a human eye.

FIG. 1 is a schematic view showing a portion of an eye 20. A reflection on the outer surface of the cornea 22 of the eye is visible in FIG. 1. Cornea 22 encloses an anterior chamber 24 of eye. The iris 26 of the eye is visible through the cornea and anterior chamber. Anterior chamber 24 is filled with aqueous humor which helps maintain the generally hemispherical shape of the cornea. The structures that drain aqueous humor from anterior chamber 24 include Schlemm's canal 30 and a large number of veins 28.

In FIG. 1, Schlemm's canal 30 can be seen encircling iris 26. Aqueous humor exits anterior chamber 24 and enters Schlemm's canal 30 by flowing through a trabecular mesh 32. Aqueous humor exits Schlemm's canal 30 by flowing through a number of outlets called collector channels 40. After leaving Schlemm's canal 30, aqueous humor travels through veins 28 and is absorbed into the blood stream.

Figure 2:
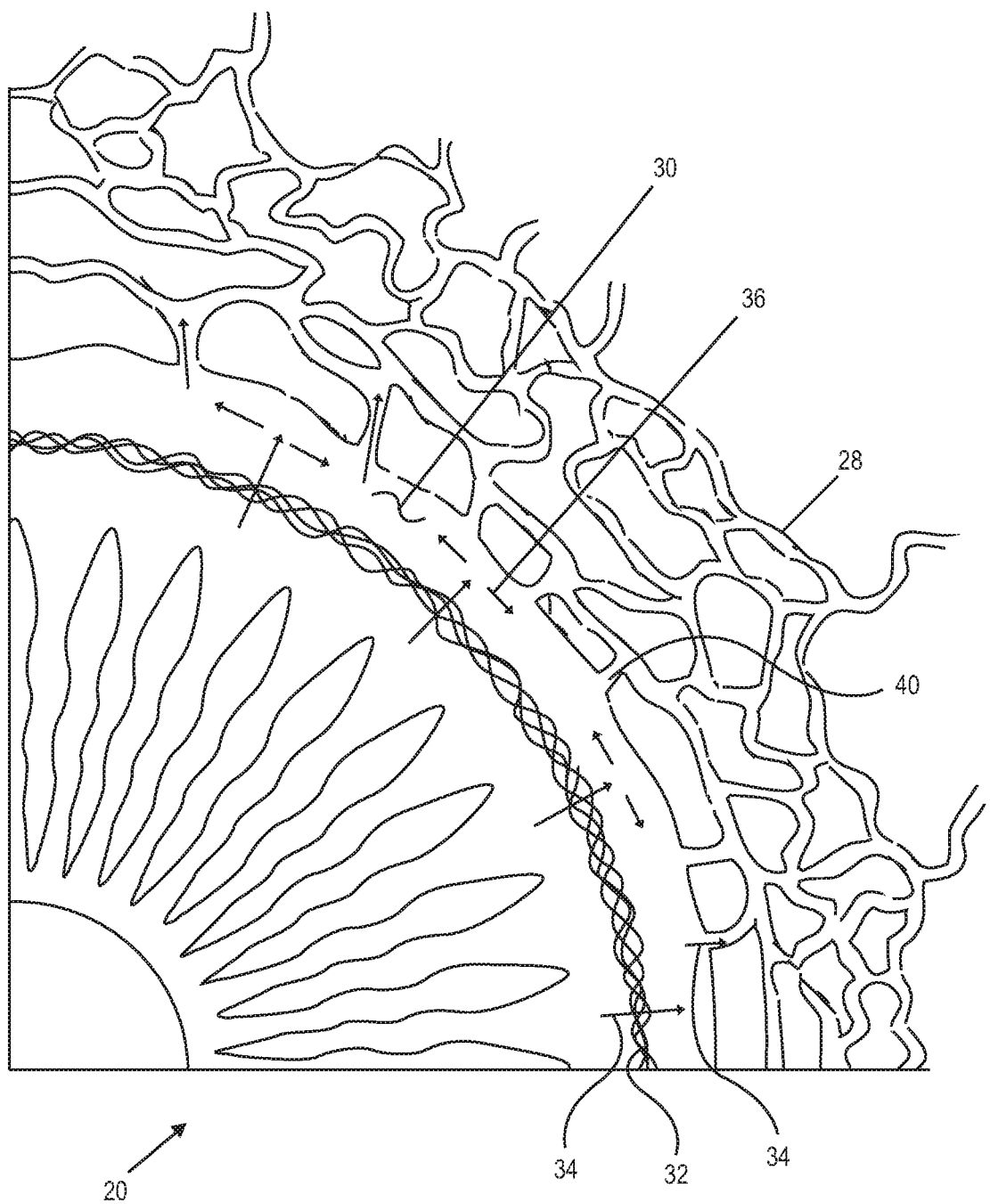
FIG. 2 is a close-up view of the eye showing Schlemm's canal.

FIG. 2 is an enlarged schematic view of a portion of eye 20 shown in the previous figure. The flow of aqueous humor in eye 20 is illustrated using arrows in FIG. 2. In FIG. 2, aqueous humor flowing through trabecular mesh 32 and into Schlemm's canal 30 is represented by a number of lateral flow arrows 34. The flow of aqueous humor along the length of Schlemm's canal is illustrated using a number of axial flow arrows 36.

Figure 3:
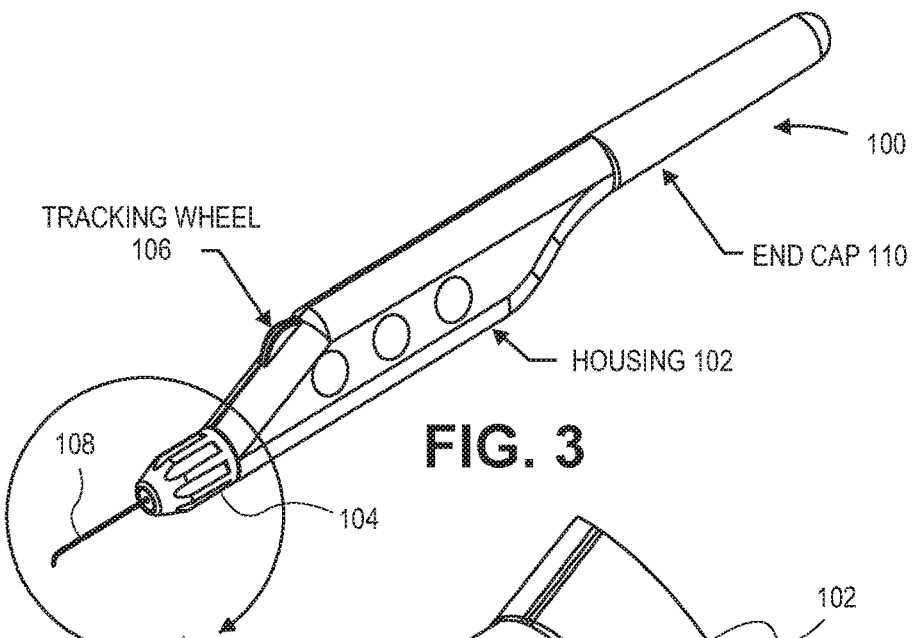
FIG. 3 is a delivery device for implanting an ocular implant in an eye.

FIG. 3 illustrates a single operator delivery device 100 configured to deliver an ocular implant into the eye of a patient, such as into Schlemm's canal, the trabecular meshwork, the suprachoroidal space, and/or the anterior chamber of the eye. The ocular implant to be implanted can include any ocular implant described in U.S. application Ser. Nos. 11/860,318, 11/943,289, 12/236,254, 12/398,847, and U.S. Provisional Patent Appln. Nos. 61/033,746, 61/120,222, and 61/120,295.

Referring to FIG. 3, delivery device 100 can include housing 102, rotatable sleeve 104, tracking wheel 106, cannula 108, and end cap 110. The delivery device shown in FIG. 3 is configured to be gripped with one hand while providing control of rotation and orientation of the cannula (via the rotatable sleeve 104) in addition to control over advancement, retraction, and deployment of the ocular implant (via the tracking wheel 106), all while gripping the delivery device with the same hand. In general, the tracking wheel is a delivery mechanism configured for advancement and retraction of the ocular implant and the rotatable sleeve is an orientation mechanism configured to control rotation and orientation of the cannula. The housing of delivery device 100—in particular, the relative location of the movable control elements within the housing—results in an ideal ergonomic relationship of the finger-operated control elements relative to the hand-stabilized housing. This design provides a configuration that will allow a user, such as a physician, to stabilize and orient the delivery device while simultaneously allowing the middle or index finger to move independently and perform the implantation of an ocular implant. This one-handed operation leaves the physician's other hand free for other uses, such as holding a gonioscope.

Figure 4:
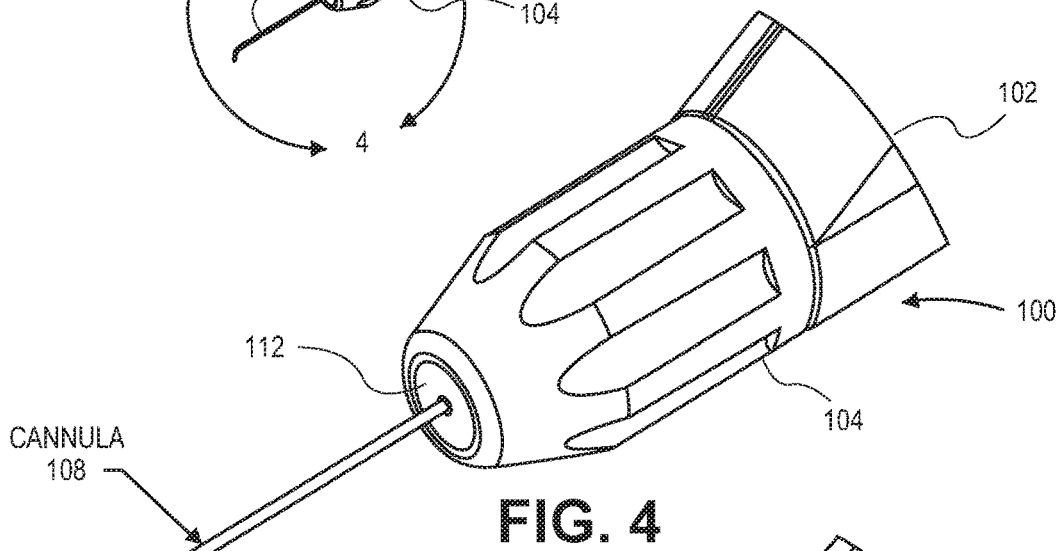
FIGS. 4 and 5 are close-up views of a portion of the delivery device.
Figure 5:
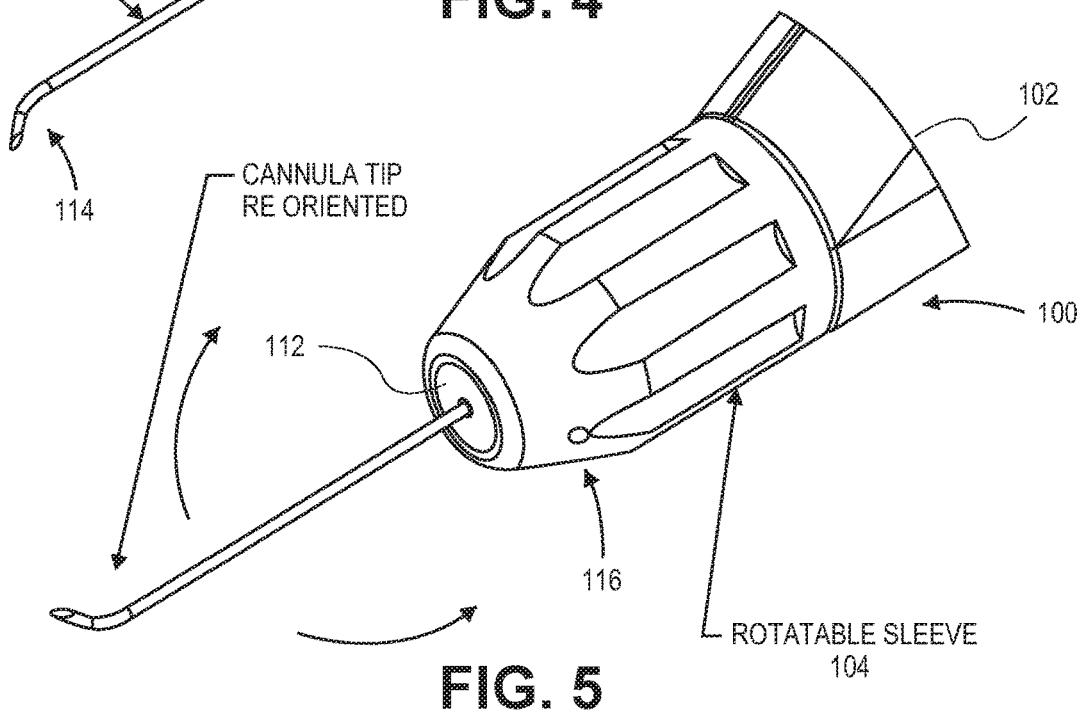

FIGS. 4-5 show a close-up view of rotatable sleeve 104 and cannula 108. In some embodiments, the cannula can have a curved or bent distal portion 114 configured to aid with implantation of an ocular implant into the eye, such as into Schlemm's canal. The bent distal portion of the cannula may have a pre-formed bend or curvature that is sized and configured to align with and be implanted in the natural curvature of Schlemm's canal. The cannula may also have a sharpened or beveled tip, for example, to cut into and through tissue. As shown, cannula can mount to a hub 112. The hub can attach to the rotatable sleeve in a number of ways, such as by a pin 116 or by an adhesive. By coupling the rotatable sleeve 104 to the cannula 108 and hub 112, rotation of the rotatable sleeve (such as by a physician) can change the orientation of the cannula with respect to the housing 102. For example, FIG. 4 shows the cannula in a first orientation, and FIG. 5 shows the cannula in a second orientation after rotation of the rotatable sleeve. The rotatable sleeve 104 may also include gripping features, such as grooves (as shown), a rubber coating, or other frictional surfaces on the rotatable sleeve.

During implantation of an ocular implant, correct alignment between the cannula and iris is necessary to ensure that the ocular implant is advanced at the correct trajectory relative to Schlemm's canal or other anatomy in the eye into which the ocular implant is to be implanted. Changing the orientation of the cannula with respect to the housing allows the delivery device 100 to be adjusted to accommodate individual anatomical variables, individual physician holding position preferences, and right/left handed users. The delivery device is configured in a manner that keeps the ocular implant aligned within the delivery device during rotation. All components are keyed together to ensure that the implant and cannula rotate as a single body while simultaneously allowing linear movement (i.e., advancement and retraction) of the ocular implant. For example, in some embodiments of an ocular implant, certain features of the implant, such as openings in the implant, are configured to be aligned with specific anatomy, such as collector channels of Schlemm's canal. Since the delivery device described herein keeps the ocular implant aligned with a predetermined curvature of the cannula, a physician can ensure the proper orientation of the implant once it's been delivered to Schlemm's canal.

Figure 6:
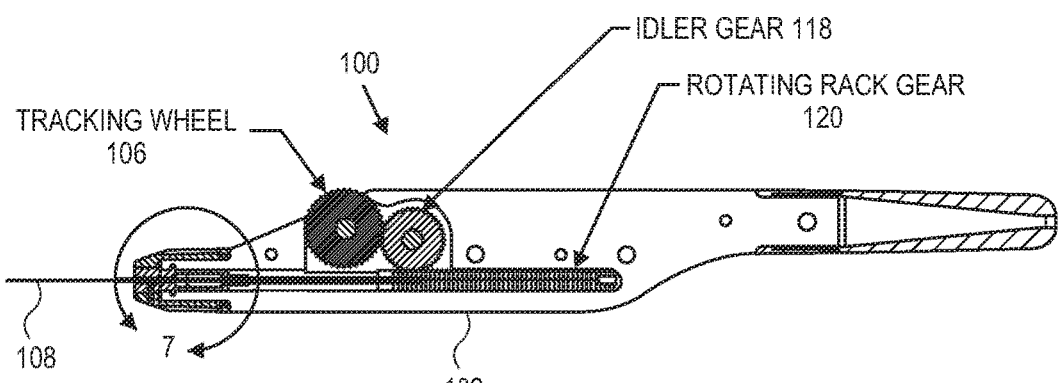
FIG. 6 is a cutaway side view of the delivery device.

FIG. 6 is a cutaway view of the delivery device 100 showing the device's internal features, including tracking wheel 106, idler gear 118, and rotating rack gear 120. Tracking wheel 106 and idler gear 118 are rotatably mounted to the housing 102. Gears on the tracking wheel engage with gears on the idler gear 118, which in turn engage with gears on the rotating rack gear 120 to move the rack gear proximally and distally within the delivery device. The idler gear 118 is included in the device so that rotation of the tracking wheel 106 in the distal direction will cause the rack gear to move distally, and rotation of the tracking wheel in the proximal direction will cause the rack gear to move proximally. In addition, the rotating rack gear 120 is configured to rotate with rotatable sleeve 104 while maintaining the ability to move linearly in the distal and proximal directions before, during, and after rotation.

Figure 7:
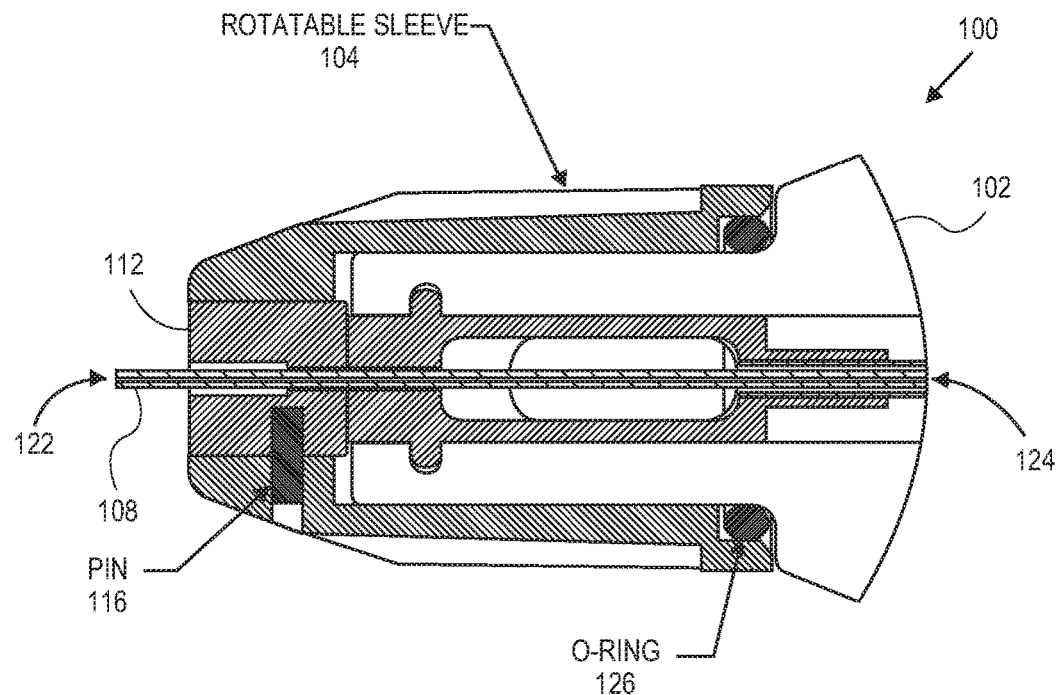
FIG. 7 is a close-up cutaway side view of the delivery device.

FIG. 7 is a close-up view of the internal features of the delivery device near the rotatable sleeve 104, including hub 112, pin 116, ocular implant 122, push tube 124, and O-ring 126. The ocular implant and push tube can be any ocular implant and push tube as described in the US Patent Applications and Provisional Patent Applications reference above. As shown in FIG. 7, the ocular implant can be positioned partially within cannula 108 and can abut push tube 124 in the delivery device. The O-ring can provide tension and resistance to the rotatable sleeve for tactile feedback during rotation and can prevent the sleeve from being moved from the desired orientation.

Figure 8:
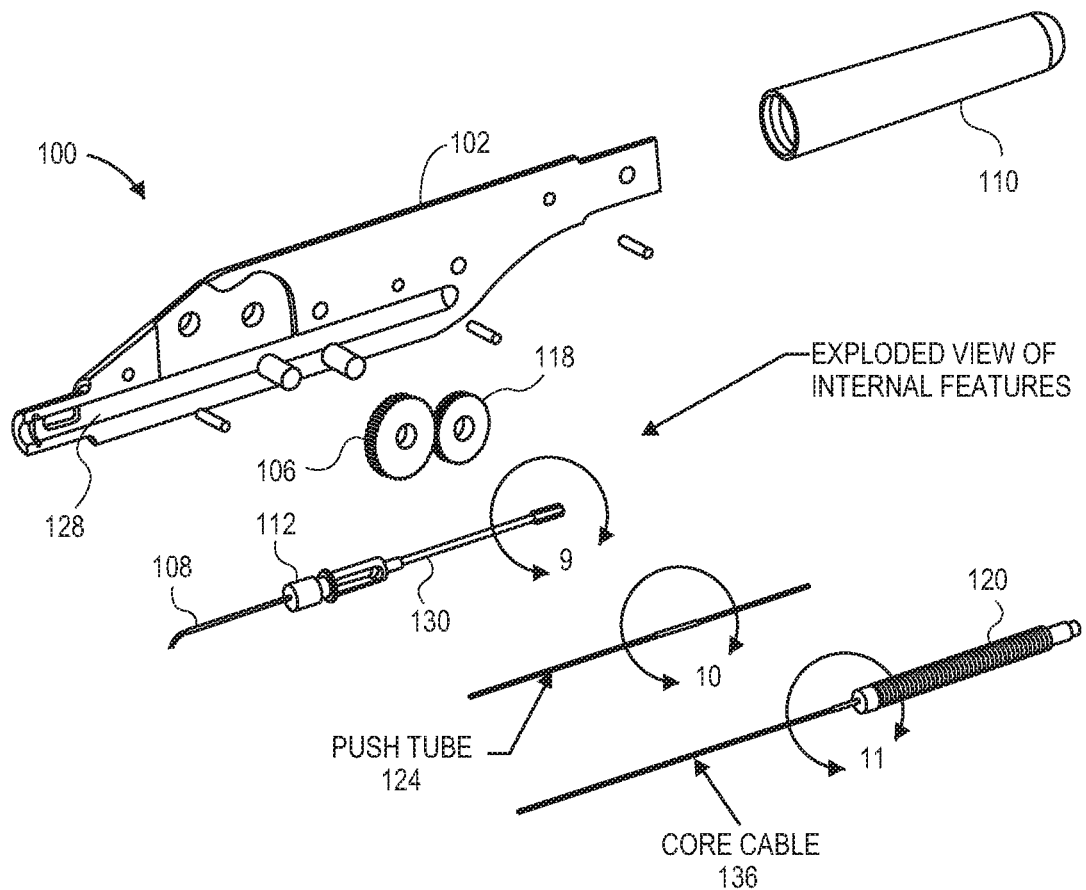
FIG. 8 is an exploded view showing the internal features of the delivery device.
Figure 9:
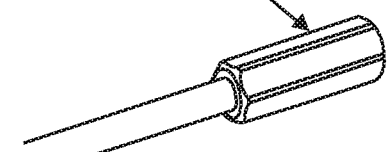
FIGS. 9, 10 and 11 are close-up views of some internal features of the delivery device.
Figure 10:
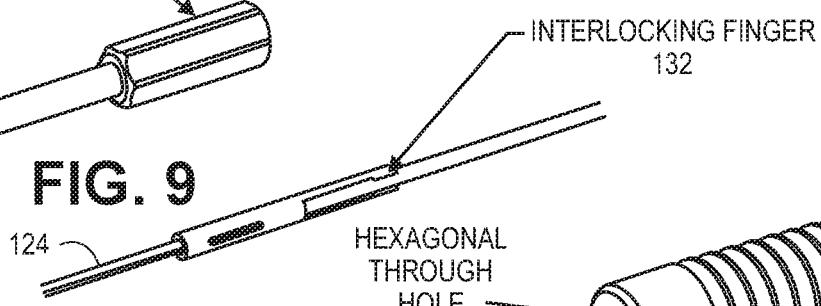
Figure 11:
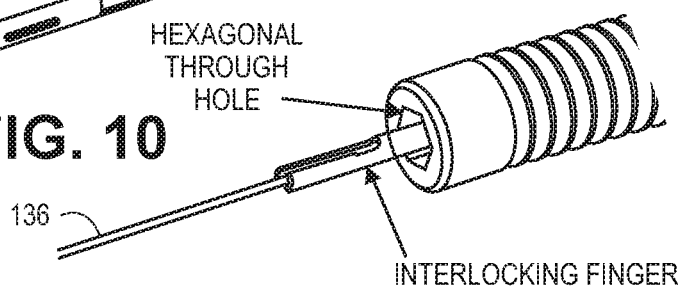

FIGS. 8-11 are exploded views of the internal features of delivery device 100, including housing 102, tracking wheel 106, cannula 108, end cap 110, hub 112, idler gear 118, rotating rack gear 120, push tube 124, slot 128, transport tube 130, interlocking finger connector 132, finger receptacle 134, and core cable or core shaft 136. As shown in FIG. 8, transport tube 130 is connected to hub 112 and is sized to slidably carry an ocular implant and push tube 124 therein. A proximal portion of the transport tube (as shown in FIG. 9) can include a hexagonal sleeve sized to fit within a hexagonal through-hole in the rotating rack gear 120 (as shown in FIG. 11).

As described herein and in the above referenced applications, push tube 124 and the ocular implant can be sized and configured to slide within transport tube 130 and a cannula. The push tube 124 can have a diameter corresponding to the diameter of the ocular implant, so that distal movement of the push tube can push against and cause distal movement of the ocular implant within the delivery system and into the patient.

Furthermore, the delivery device can also include a core cable 136 sized to slide within the ocular implant and push tube 124. Referring to FIGS. 8 and 11, the core cable 136 can be coupled to the rotating rack gear 120. As described in the above referenced applications, the core cable can be positioned within an internal diameter of the ocular implant during delivery of the implant so as to block and prevent any sharp edges or holes in the implant (such as the edges of fluid inlets and outlets in the implant) from cutting or damaging tissue within the patient during implantation. Additionally, the core can have a distal radius adapted to dilate Schlemm's canal as the implant is inserted into the patient.

As shown in FIGS. 10-11, a proximal portion of the core cable can include interlocking finger receptacles 134 adapted to engage and join interlocking fingers 132 on a proximal portion of the push tube. The interlocking fingers 132 can be pre-biased to assume an expanded or outward configuration. For example, the interlocking fingers 132 can be formed from stainless steel or from a shape memory material such as Nitinol. In some embodiments, the interlocking finger receptacles and the interlocking fingers are cut from hypotubes having the same diameter. When the fingers are compressed, such as within transport tube 130, they can engage the interlocking finger receptacles to join the push tube and core cable together, and allow the push tube and core cable to move together through the transport tube 130 and delivery system as the rotating rack gear is moved distally and proximally.

Figure 12:
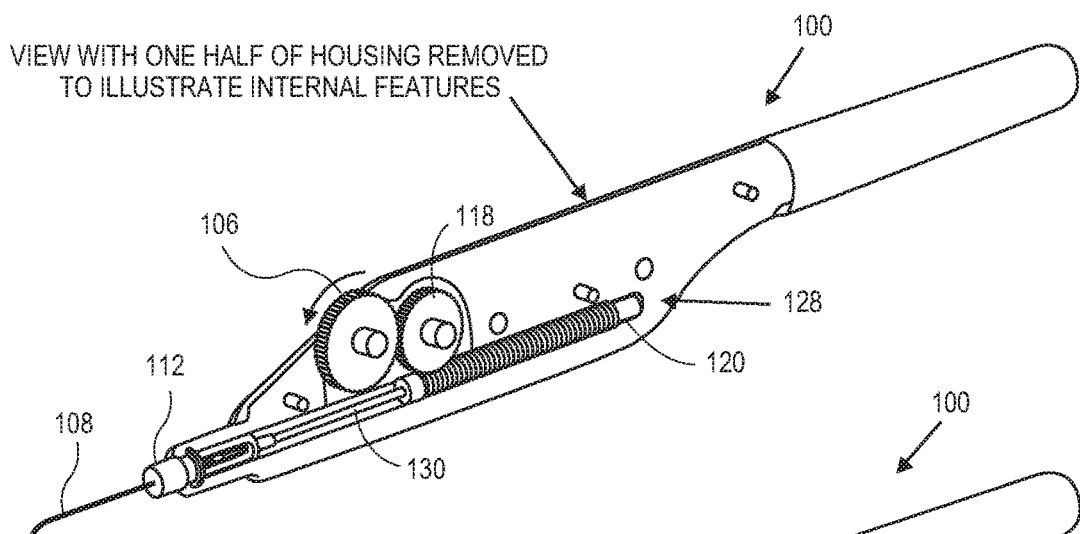
FIGS. 12 and 13 are cutaway side views of the delivery device.
Figure 13:
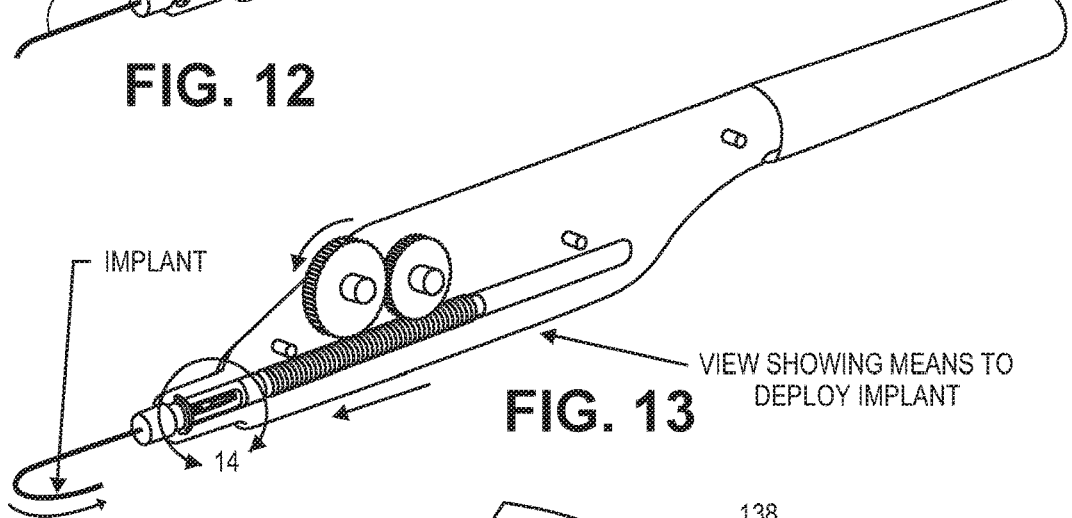

FIGS. 12-13 illustrate how rotation of the tracking wheel 106 causes the movement of idler gear 118, rotating rack gear 120, ocular implant, push tube 124, and core cable 136, thereby enabling one-handed operation through one-fingered advancement of the implant, release of the implant and retraction of the delivery mechanism. In FIG. 12, delivery device 100 is shown prior to deployment of the ocular implant into the patient, with rotating rack gear 120 positioned proximally within slot 128 in housing 102. FIG. 13 shows the delivery device fully deployed, with the rotating rack gear positioned distally in slot 128 and touching hub 112. To move the rotating rack gear 120 from the proximal position shown in FIG. 12, to the distal position shown in FIG. 13, the tracking wheel 106 can be rotated distally (e.g., in a counter-clockwise direction as shown by the arrows in FIG. 13), which causes idler gear 118 to rotate in a proximal direction, which in turn causes the rotating rack gear 120 to move distally towards hub 112. Similarly, the rotating rack gear can be returned to the proximal position within housing 102 by rotating tracking wheel 106 in a proximal direction. In another embodiment, the idler gear can be eliminated from the delivery device, which would cause distal movement of the tracking wheel to move the rack gear proximally.

As the rotating rack gear 120 moves distally from the proximal position in FIG. 12 to the distal position in FIG. 13, the rack gear causes push tube 124, core cable 136, and the ocular implant (not shown) to move distally within transport tube 130. When the rack gear is in the distal position as shown in FIG. 13, the ocular implant is pushed completely out of cannula 108 and into the patient. In some embodiments, the rack gear need not be fully advanced in the distal-most position to push the implant out of the cannula.

Figure 14:
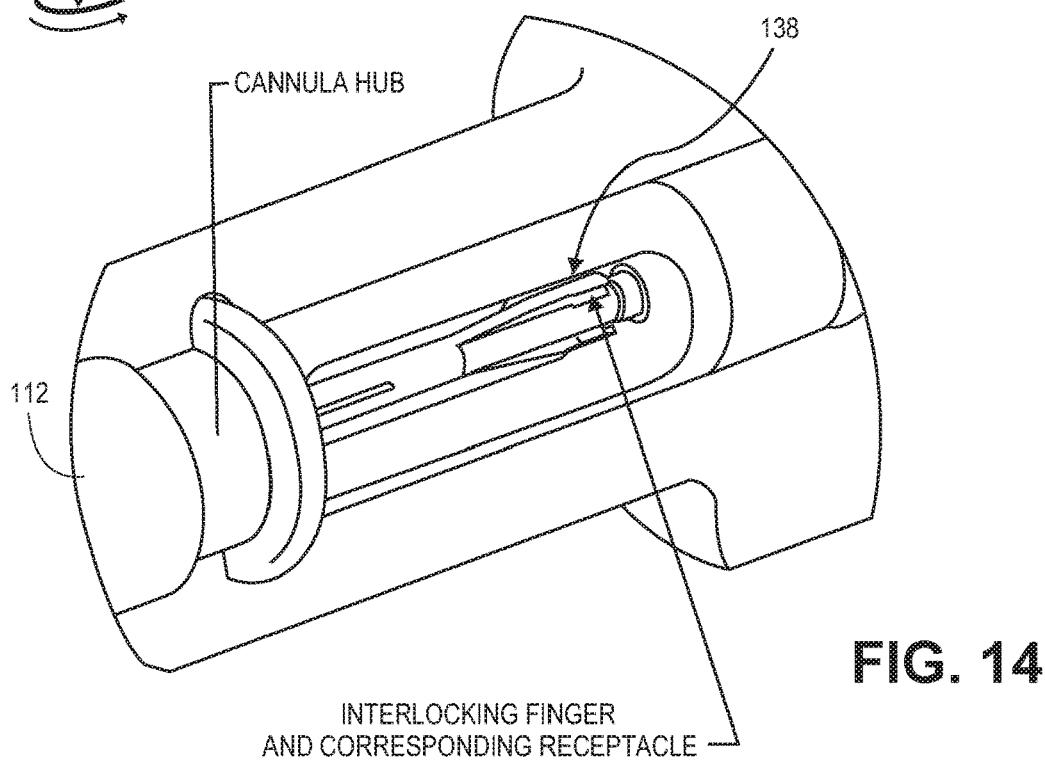
FIG. 14 is a close-up cutaway side view of a portion of the delivery device.

Additionally, when the rack gear is in the distal-most position, the interlocking fingers 132 (show in FIG. 14) of the push tube 124 and the interlocking finger receptacles 134 (show in FIG. 14) of the core cable 136 are positioned in an opening 138 in hub 112, as shown in FIG. 14. The opening 138 can have a larger inner diameter than the transport tube 130. The transport tube 130 can terminate at the opening 138, so when the interlocking fingers enter the opening and are no longer constrained by the inner walls of the transport tube, the interlocking fingers 132 are allowed to automatically expand outward to assume their pre-biased configuration, thereby disengaging the push tube 124 from the finger receptacles 134 of the core cable 136. With the core cable detached from the push tube, proximal movement of the rack gear (such as by rotating the tracking wheel in a proximal direction) can remove the core cable proximally from the push tube and ocular implant, thereby removing the core cable from the implant and leaving the implant in the patient. The push tube is allowed to remain at the distal-most position to abut the ocular implant and keep the implant in place as the core cable is removed.

It should be understood that the advancement and retraction of the ocular implant are not limited to the tracking wheel described herein. For example, in some embodiments, the housing may include buttons and a motor for electronically driving the wheel to advance and retract the implant.

Figure 15:
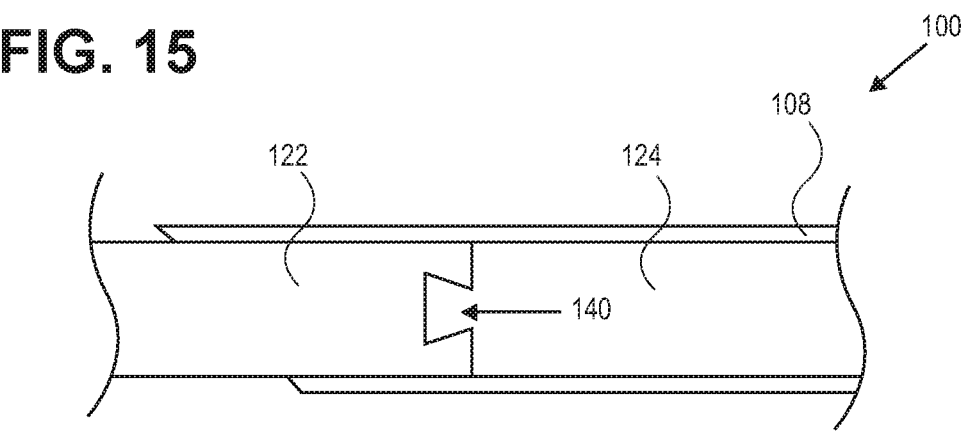
FIGS. 15, 16 and 17 illustrate one embodiment of detaching an ocular implant from the delivery device.
Figure 16:
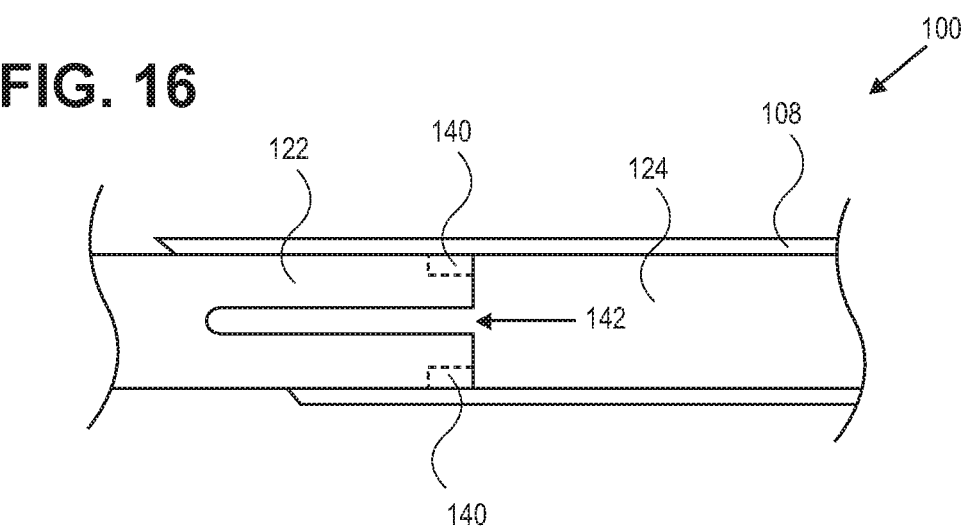
Figure 17:
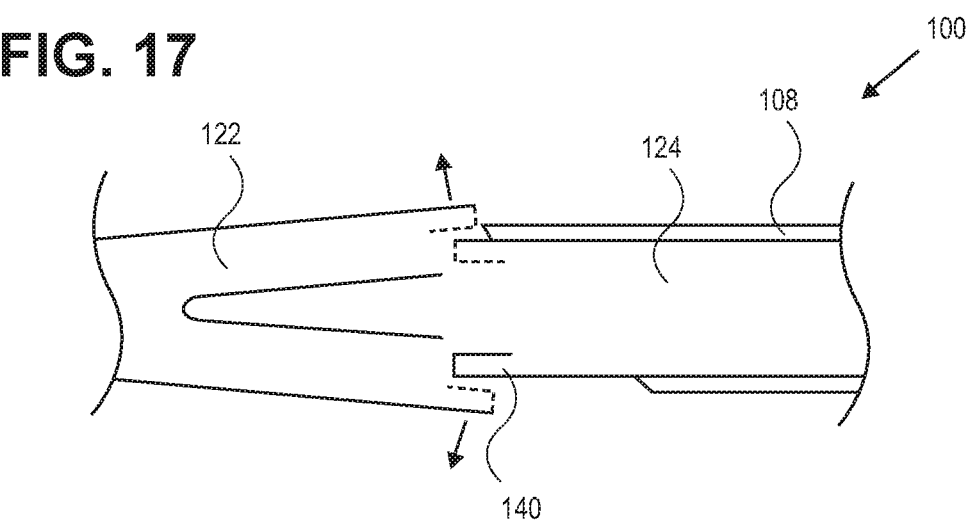

FIGS. 15-17 illustrate an embodiment of a device and method for selectively coupling an ocular implant 122 to a push tube 124 in a delivery device 100. FIG. 15 is a top down view of push tube 124 and ocular implant 122 positioned within cannula 108 of delivery device 100. The push tube and ocular implant can include an interlocking component 140, similar to the interlocking fingers and interlocking finger receptacles described above. For example, the push tube may include an interlocking finger and the ocular implant may include an interlocking finger receptacle, or vice versa. Any variety of interlocking shapes may be used. FIG. 16 is a side view of the push tube and ocular implant shown in FIG. 15. FIG. 16 shows the ocular implant further comprising a slit or plurality of slits 142. The ocular implant can be pre-biased to assume an expanded configuration. When the implant is compressed, such as within the cannula or the transport tube described above, the interlocking component 140 will compress and cause the implant to engage and lock with the push tube. However, when the ocular implant is pushed distally beyond the distal tip of the cannula 108, as shown in FIG. 17, the implant can assume its pre-biased configuration, causing the implant to automatically expand along the slits and detach from the push tube to be released in the patient. The expanded portion of the implant also provides for a larger opening to prevent clogging when implanted inside a patient.

Figure 18:
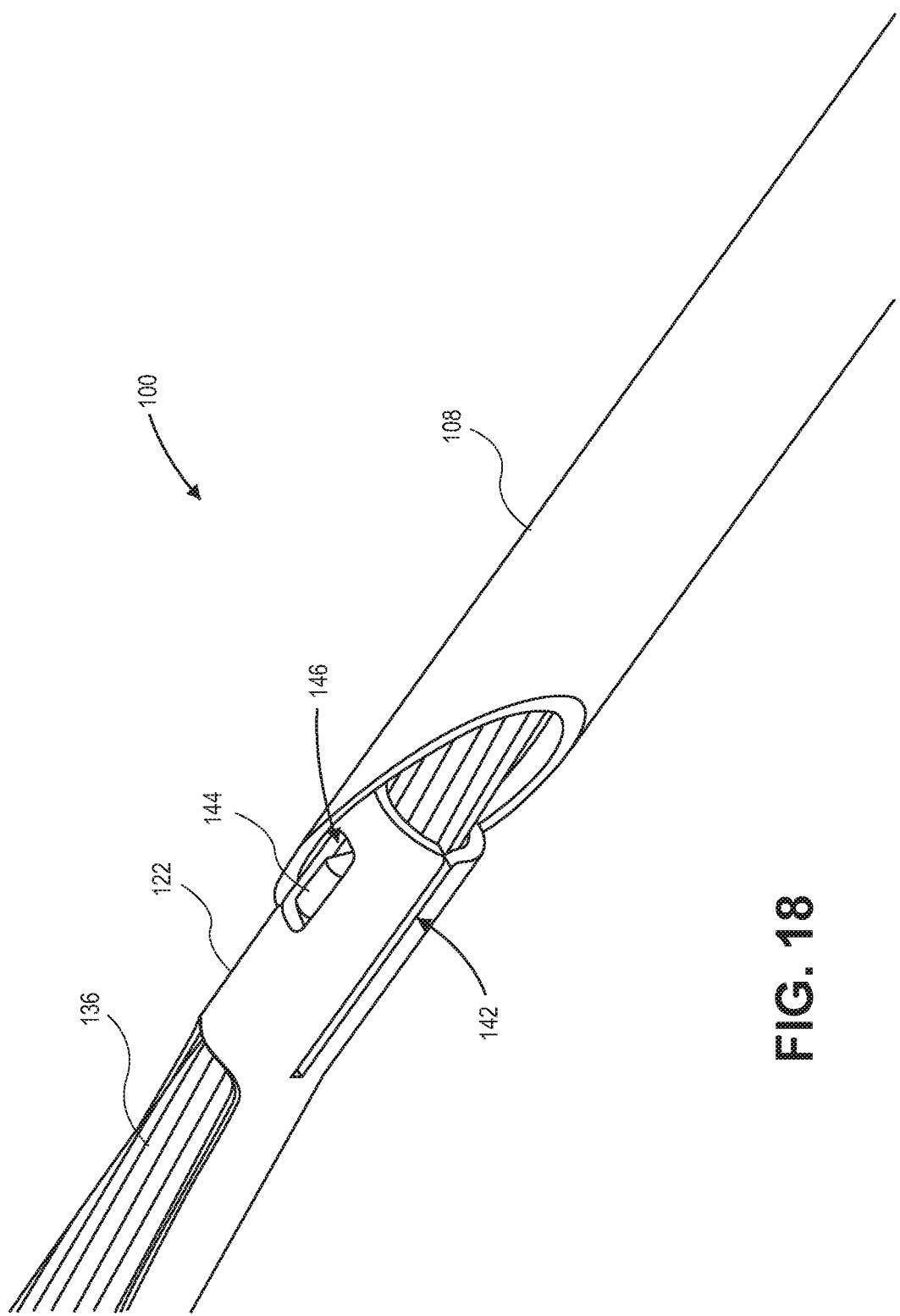
FIGS. 18 and 19 illustrate another embodiment of detaching an ocular implant from the delivery device.
Figure 19:
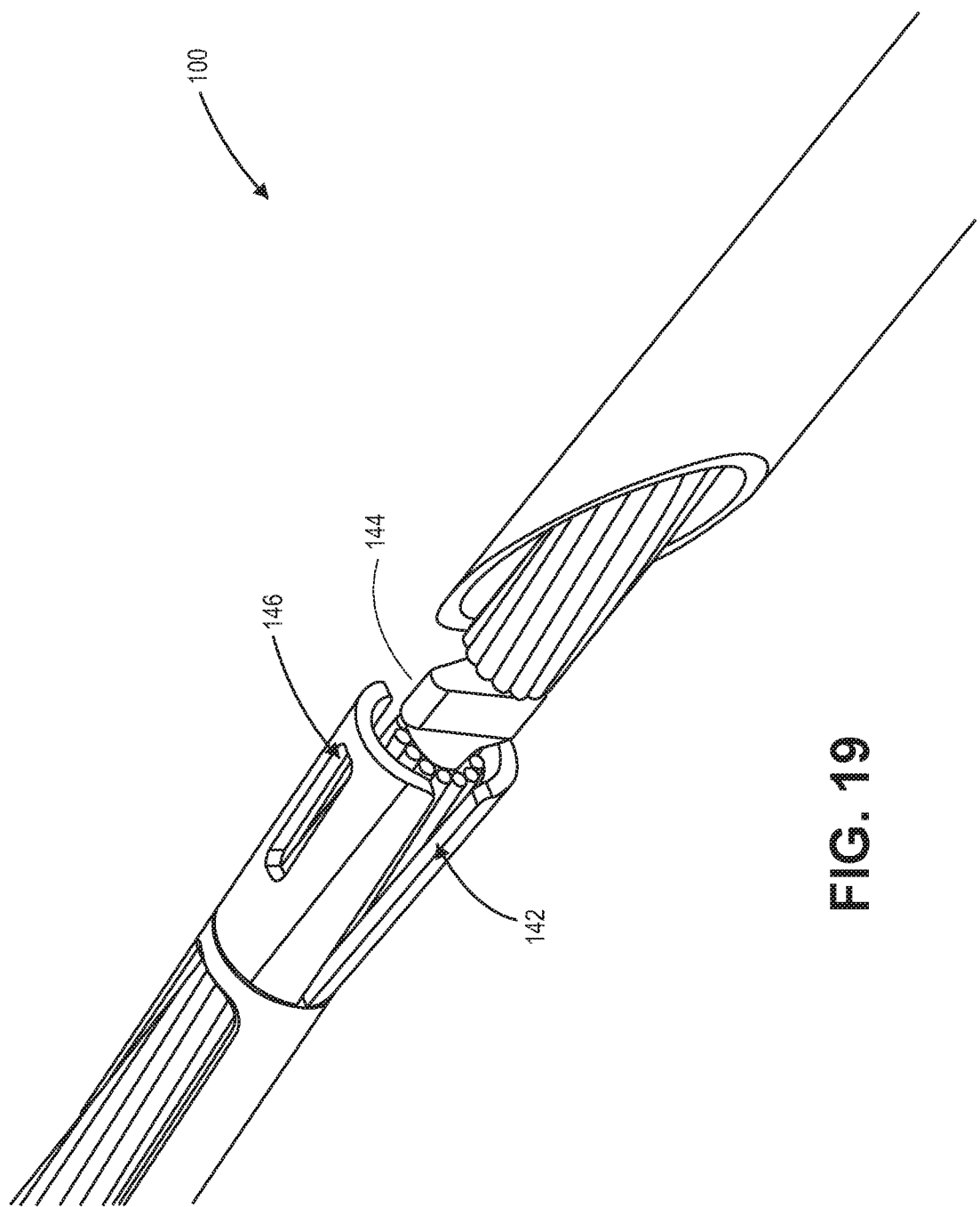

FIGS. 18-19 illustrate an alternative embodiment of the delivery system 100 that does not include a push tube, but rather uses a locking key 144 coupled to the core cable 136 to advance, retract, and deliver the ocular implant into a patient. As shown in FIG. 18, core cable 136 can be disposed within the ocular implant 122 and cannula 108 of delivery system 100. Locking key 144 can be disposed on the core cable and can engage window 146 in the ocular implant. As described above, the implant can be pre-biased to assume an expanded configuration when the implant is not constrained (e.g., such as when the implant is not constrained within a cannula). When the implant is compressed, such as within the cannula or the transport tube described above, the locking key 144 will engage window 146 to couple the core cable to the implant. However, when the ocular implant is pushed distally beyond the distal tip of the cannula 108, as shown in FIG. 19, the implant can assume its pre-biased configuration, causing the implant to expand and detach from the core cable.

The delivery devices described herein are configured to advance and retract an ocular implant and deliver the implant into the eye of a patient by a physician using a single hand. A physician typically has only one hand available to perform the implantation as the other hand is used to simultaneously hold and stabilize a gonioscope for visualization of the implantation procedure. Physicians typically use their feet during the procedure to adjust the image through the surgical microscope, making a foot-operated system impractical.

As described above, advancement and retraction of the implant can be controlled with a tracking wheel 106, and orientation of the implant in the patient can be controlled by changing the orientation of the cannula, hub, implant, push tube, and core cable by rotating the rotatable sleeve 104. When the ocular implant is advanced distally beyond the distal tip of cannula 108, the implant can automatically expand to a pre-biased configuration to disengage the push tube and remain within the patient in the desired location within the eye. As described above, it may be necessary to remove a core cable from within the implant by retracting the rotating rack gear in the proximal direction before fully implanting the ocular implant in the patient.

Figure 20:
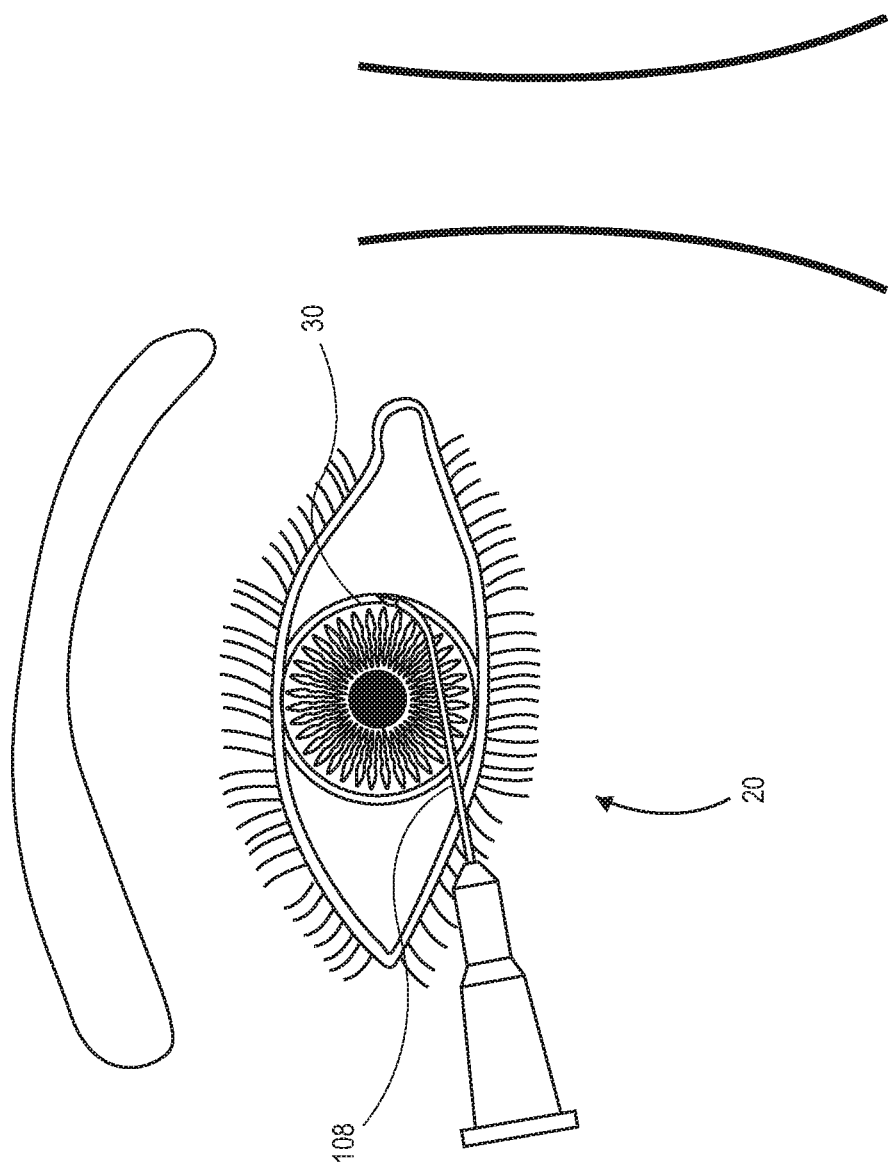
FIGS. 20, 21 and 22 illustrate a method for implanting an ocular device in an eye of a patient.
Figure 21:
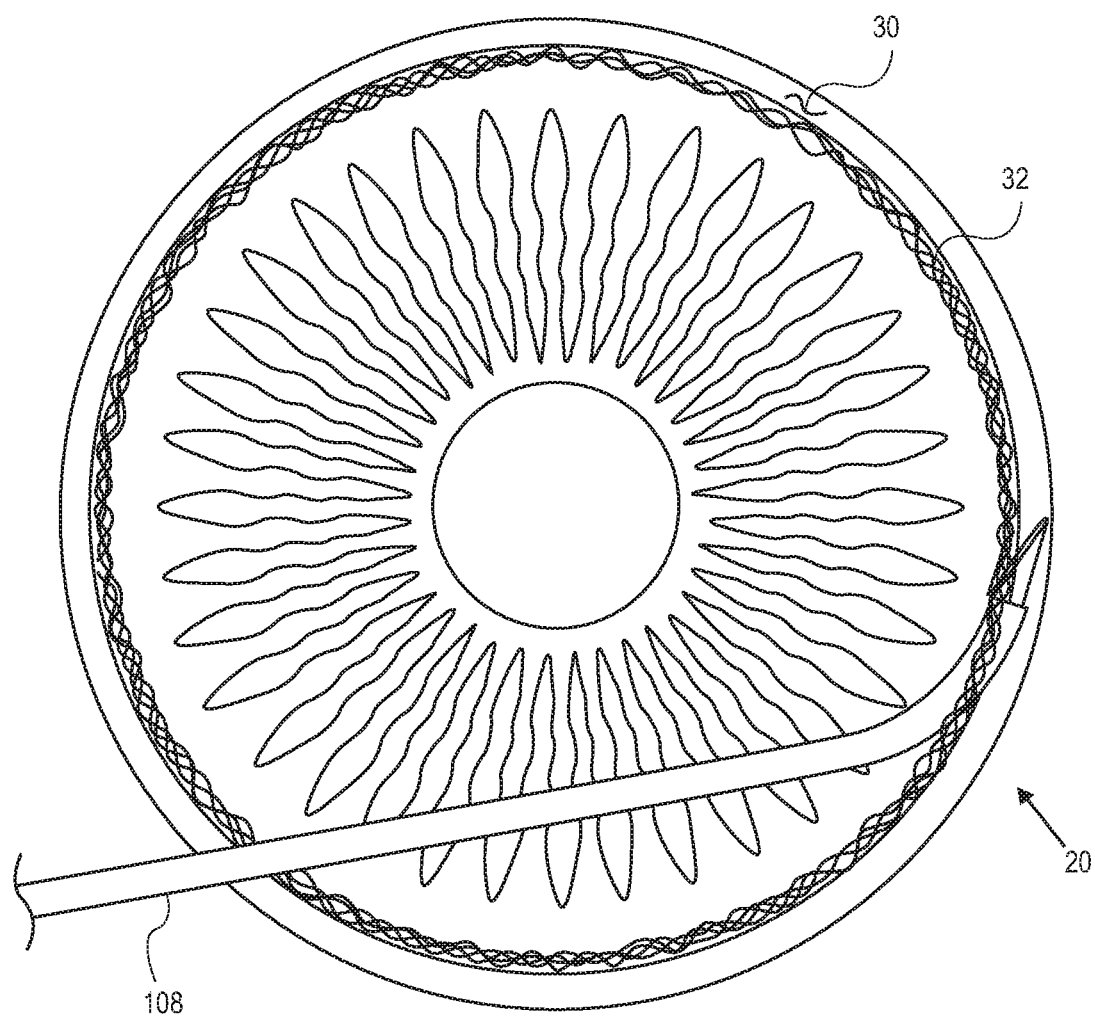
Figure 22:
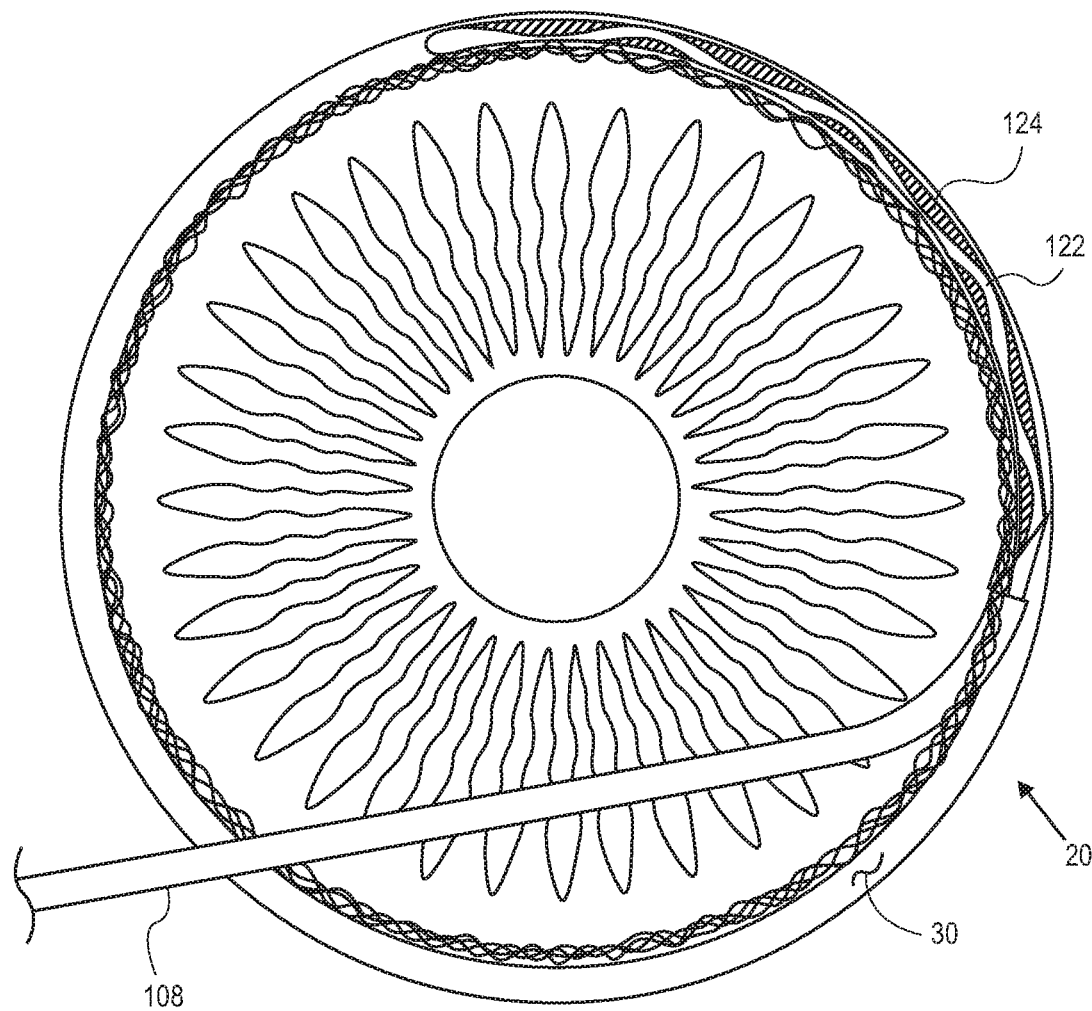

FIGS. 20-22 illustrate a method for delivering an ocular implant into a patient. The ocular implant may be inserted into Schlemm's canal, the trabecular meshwork, the suprachoroidal space, and/or the anterior chamber to facilitate the outflow of aqueous humor from the anterior chamber. This flow of aqueous humor can include axial flow along Schlemm's canal, flow from the anterior chamber into Schlemm's canal, flow leaving Schlemm's canal via outlets communicating with Schlemm's canal, or flow into the suprachoroidal space. When implanted within the eye, the ocular implant will support trabecular mesh tissue and Schlemm's canal tissue and will provide for improved communication between the anterior chamber and Schlemm's canal (via the trabecular meshwork), between pockets or compartments along Schlemm's canal, or between the anterior chamber and the suprachoroidal space.

FIG. 20 is a view showing a portion of the face and eye 20. Cannula 108 extends through a cornea of eye 20 so that the distal end of cannula 108 is disposed in the anterior chamber of the eye. With reference to FIG. 20, it will be appreciated that the distal tip of cannula 108 is positioned near the trabecular mesh and Schlemm's canal 32 of the eye. The orientation of the cannula to the eye can be adjusted by rotating the rotatable sleeve described above with reference to FIGS. 3-7.

FIG. 21 is a further enlarged view illustrating a portion of eye 20 shown in the previous figure. In the embodiment of FIG. 21, the distal tip of cannula 108 has pierced through trabecular mesh 32. The distal tip of cannula 108 has also pierced the wall of Schlemm's canal 30 and a distal opening of cannula 108 is disposed in fluid communication with Schlemm's canal. In some embodiments, cannula 108 is curved to achieve substantially tangential entry into Schlemm's canal.

FIG. 22 is an additional view of eye 20 shown in the previous figure. In the embodiment of FIG. 22, an ocular implant 122 has been advanced through the cannula and into Schlemm's canal of the eye. FIG. 22 illustrates a core cable 124 disposed within the implant 122, and push tube (not shown) abutting a proximal portion of the ocular implant within the cannula 108, as described above. The ocular implant can be advanced through the delivery system and into the eye with the delivery device 100 described herein, such as by rotating tracking wheel 106 to advance the push tube, core cable, and implant through the delivery system and into the eye, as described above with reference to FIGS. 3, 6, and 12-13.

Once the implant is positioned within Schlemm's canal (or alternatively within the suprachoroidal space or other anatomy of the eye), the implant can be advanced beyond a distal portion of the cannula to allow the implant to detach from the push tube and core cable (as described above and shown in reference to FIGS. 14-19). The core cable can also be configured to automatically detach from the push tube, and the core cable can then be retracted from the ocular implant while the push tube is allowed to abut the implant to keep the implant in place. Once the implant is within the eye of the patient, the delivery system can be removed from the patient leaving only the implant behind.

In another embodiment that does not utilize a push tube, as described above and referenced in FIGS. 18-19, the implant can be advanced beyond a distal portion of the cannula to allow the implant to detach from the a locking key of the core cable. The core cable can then be removed from the ocular implant. Once the implant is within the eye of the patient, the delivery system can be removed from the patient leaving only the implant behind.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of delivering an implant into an eye of a patient, comprising:
   inserting a delivery device into Schlemm's canal of the eye;
   advancing the implant into the eye through the delivery device and past a distal tip of the delivery device; and
   expanding the implant to disengage the implant from the delivery device, wherein the implant automatically expands to disengage itself from the delivery device when it is advanced past the distal tip of the delivery device.

2. The method of claim 1 wherein the delivery device comprises a cannula.

3. The method of claim 2 further comprising the step of adjusting an orientation of the cannula with an orientation mechanism to align the cannula with a curvature of Schlemm's canal.

4. The method of claim 3 wherein the advancing step and the adjusting step are achieved with a single-hand of a user.

5. The method of claim 1 wherein the advancing step further comprises advancing the implant with a wheel disposed on the delivery device.

6. The method of claim 1 wherein the expanding step further comprises expanding the implant to disengage an interlocking component of the implant from an interlocking component of the delivery device.

7. The method of claim 6 wherein the interlocking component of the delivery device is an interlocking component of a push tube.

8. The method of claim 6 wherein the interlocking component of the delivery device is an interlocking component of a core cable.

9. The method of claim 1 wherein the advancing step further comprises advancing the implant into the eye with a push tube.

10. The method of claim 1 wherein the advancing step further comprises advancing the implant into the eye with a core cable.

11. The method of claim 10 further comprising removing the core cable from the implant after expanding the implant.

12. A method of implanting an ocular implant into Schlemm's canal of an eye, comprising:
   rotating an orientation mechanism of a delivery device to align a cannula with Schlemm's canal;
   advancing the cannula through a corneal incision and into the eye;
   piercing Schlemm's canal with the cannula;
   controlling an advancement mechanism of the delivery system with a first hand to advance the ocular implant from the delivery system into Schlemm's canal;
   holding a gonioscope with a second hand during the controlling step to visualize implantation of the ocular implant into Schlemm's canal; and
   automatically expands to disengage the ocular implant from the delivery system when the ocular implant is advanced beyond a distal tip of the cannula.

13. The method of claim 12 further comprising expanding the ocular implant in the eye to disengage the ocular implant from the delivery system.

* * * * *